United States Patent
Stemmer

(10) Patent No.: US 9,261,575 B2
(45) Date of Patent: Feb. 16, 2016

(54) MAGNETIC RESONANCE METHOD AND APPARATUS FOR OBTAINING A SET OF MEASURED DATA RELATING TO A BREATHING OBJECT OF INTEREST

(71) Applicant: Alto Stemmer, Erlangen (DE)

(72) Inventor: Alto Stemmer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 233 days.

(21) Appl. No.: 13/866,341

(22) Filed: Apr. 19, 2013

(65) Prior Publication Data

US 2013/0281828 A1    Oct. 24, 2013

(30) Foreign Application Priority Data

Apr. 20, 2012 (DE) .......... 10 2012 206 550

(51) Int. Cl.
 A61B 5/055 (2006.01)
 G01R 33/567 (2006.01)
 G01R 33/48 (2006.01)

(52) U.S. Cl.
 CPC .......... G01R 33/5673 (2013.01); A61B 5/055 (2013.01); G01R 33/5676 (2013.01); G01R 33/4818 (2013.01); G01R 33/4826 (2013.01)

(58) Field of Classification Search
 CPC .......... G01R 33/4818; G01R 33/4826; G01R 33/5673; G01R 33/5676; A61B 5/055
 See application file for complete search history.

(56) References Cited

U.S. PATENT DOCUMENTS 7,039,451 B1    5/2006 Jhooti et al.
2011/0152668 A1*  6/2011 Stemmer ............ 600/413
2012/0271155 A1* 10/2012 Stemmer ............ 600/413

OTHER PUBLICATIONS

Jhooti et al., "Phase ordering with Automatic Window Selection (PAWS) with Half Fourier for Increased Scan Efficiency and Image Quality," Intl. Soc. Mag. Reson. Med., vol. 11, p. 2146, (2004).
Jhooti et al., "Phase Ordering With Automatic Window Selection (PAWS): A Novel Motion-Resistant Technique for 3D Coronary Imaging," Magnetic Resonance in Medicine, vol. 43, pp. 470-480, (2000).
Kolbitsch, "Highly Efficient Whole-Heart Imaging Using Radial Phase Encoding-Phase Ordering With Automatic Window Selection," Magnetic Resonance in Medicine, vol. 66, pp. 1008-1018, (2011).
Nuval et al., "Refined PAWS Algorithms for 3D Coronary MRA," Intl. Soc. Mag. Reson. Med., vol. 11, p. 1625, (2003).

(Continued)

*Primary Examiner* — Ruth S Smith
(74) *Attorney, Agent, or Firm* — Schiff Hardin LLP

(57) ABSTRACT

For generating a three-dimensional magnetic resonance image of a respirating examination subject, the respiration of the examination subject is divided into a number of predefined clusters. Based on a measured respiratory position of the examination subject, one of these clusters is selected. The scanned k-space range is divided into a number of data acquisition shots which, by means of a particular k-space trajectory, each fill a number of k-space lines. The different shots are acquired for the different clusters until all shots of the measurement data set are assigned together to at least two adjacent clusters. The magnetic resonance image is reconstructed from those shots that are assigned to at least two adjacent clusters.

6 Claims, 6 Drawing Sheets

(56) References Cited

OTHER PUBLICATIONS

Nuval, "An improved real-time navigator gating algorithm for reducing motion effects in coronary magnetic resonance angiography," Journal of X-Ray Science and Technology, vol. 11, pp. 115-123, (2003).

Sachs et al., "Real-Time Motion Detection in Spiral MRI Using Navigators," Magnetic Resonance in Medicine, vol. 32, pp. 639-645, (1994).

Wang et al., "Navigator-Echo-based Real-Time Respiratory Gating and Triggering for Reduction of Respiration Effects in Three-dimensional Coronary MR Angiography," Cardiac Radiology, Radiology vol. 198, pp. 55-61, (1996).

* cited by examiner

MAGNETIC RESONANCE METHOD AND APPARATUS FOR OBTAINING A SET OF MEASURED DATA RELATING TO A BREATHING OBJECT OF INTEREST

BACKGROUND OF THE INVENTION

1. Field of the Invention

A method for acquiring a measurement data set of a respiring examination subject, using magnetic resonance technology, a magnetic resonance device, computer programs, as well as electronically readable data media.

The invention relates to a method for the acquisition of a measurement data set of an examination subject by means of magnetic resonance technology, a magnetic resonance system, a computer program as well as an electronically readable data medium.

2. Description of the Prior Art

Magnetic resonance (MR) is a known technology with which images from the interior of an examination subject can be generated. Expressed simply, the examination subject is placed in a magnetic resonance imaging scanner, in a strong, static, homogenous base magnetic field, also called a $B_0$ field, having a field strength of 0.2 tesla —7 tesla and more, such that the nuclear spins of the subject orient themselves along the base magnetic field. In order to trigger magnetic resonance signals, the examination subject is irradiated with radio frequency excitation pulses (RF pulses), the triggered magnetic resonance signals are detected and entered into a memory that represents a mathematical domain known as k-space, and MR images are reconstructed on the basis of the k-space data, or spectroscopy data are determined. For the spatial encoding of the measurement data, rapidly activated magnetic gradient fields are superimposed on the base magnetic field. The recorded measurement data are digitized and stored as complex number values in a k-space matrix. From the k-space matrix populated with data values in this manner, an associated MR image can be reconstructed, for example, by means of a multi-dimensional Fourier transformation.

The respiratory movement of a patient that is to be examined by means of MR can lead to so-called ghosting, to blurring, and/or to intensity losses in the images generated, as well as registration errors between generated images particularly in an examination of the organs of the thorax and the abdomen, i.e. of examination regions affected by respiratory movement. These artifacts can make it difficult for a physician to perform an analysis on the basis of the images, and can lead to lesions being overlooked, for example. Numerous techniques exist in the prior art for reducing artifacts resulting from respiratory movement. One of these techniques is respiratory gating. Respiratory gating is a technique with which, during the MR measurement, the respiration of the patient is recorded and assigned to the acquired measurement data. With respiratory gating, only measurement data are then used for reconstruction for which the associated recorded respiratory movement fulfills certain specifiable criteria.

The patient's respiration can be detected thereby with external sensors such as, for example, a pneumatic cushion or with MR signals, so-called navigators. A navigator is usually a short sequence which acquires MR signals, for example, from the diaphragm or another signal source in the examination subject, whose movement is correlated with the patient's respiration. Via the position of the diaphragm, or other signal source, the respiratory motion can be tracked.

With respiratory gating with navigators, the navigator sequence is interlaced for example with the imaging sequence and a diaphragm position measured with a navigator is then assigned immediately thereafter (or before) to the acquired imaging data.

A distinction is made between retrospective and prospective respiratory gating.

With retrospective respiratory gating the respiratory movement is detected and recorded during the MR measurement, but not evaluated. Instead, the k-space that is to be recorded is measured repeatedly. For the reconstruction, only a portion of the measured data are referenced, preferably that data in which the respiratory signal lies within a specific window for a distinctive respiratory position. If a specific k-space data point that is necessary for the image reconstruction is repeatedly measured within the distinctive window, then the data can be averaged. If, instead, a data point is always measured outside of the window, then that data point deviating the least from the distinctive position can be used for the reconstruction.

With prospective respiratory gating, the physiological respiratory signal measured using a respiratory sensor (e.g. the diaphragm position measured with a navigator sequence) is evaluated during the measurement, and the MR measurement is controlled, based on the recorded physiological signal. In the simplest embodiment, the so-called acceptance/rejection algorithm (ARA), the measurement of an imaging data packet (and if applicable, the associated navigator sequence) is repeated until the physiological signal falls within a previously defined acceptance window.

One example of an acceptance/rejection algorithm of this type and, at the same time, the first description of respiratory gating with navigators, is described in the article by Todd S. Sachs, Craig H. Meyer, Bob S. Hu, Jim Kohli, Dwight G. Nishimura and Albert Macovski: "Real-Time Motion Detection in Spiral MRI Using Navigators," MRM 32: Pages 639-645 (1994). The authors acquired one or more navigators for each excitation of a spiral sequence. The navigators were acquired here following the acquisition of the image data. Different navigators are distinguished by their spatial orientation. From each navigator, a spatial displacement along the axis of the navigator in relation to a reference navigator is calculated using a cross-correlation. The navigator scan acquired following the first imaging scan is used, in each case, as a reference. A specific imaging scan is repeated until the spatial displacement determined with the navigator, in relation to the reference, is less than a threshold value provided by a user. This, therefore, relates to an acceptance/rejection algorithm based on one or more spatial displacements.

Another example of an acceptance/rejection algorithm is described by Wang et al. in "Navigator-Echo-Based Real-Time Respiratory Gating and Triggering for Reduction of Respiratory Effects in Three-Dimensional Coronary MR Angiography," Radiology 198; Pages 55-60 (1996). In this case, the physiological signal is the displacement of the diaphragm position, determined with a navigator, in relation to a reference state. One difference from the work by Sachs et al. is that, in each case, a navigator is acquired before and after the imaging scan, and that the imaging scan is then only accepted if the displacement determined by means of both navigators is less than the threshold value.

In order to determine the acceptance window, a so-called pre-scan is normally carried out for each patient, in which the respiratory movement is recorded, for example, with the navigator sequence, but imaging data are not yet acquired.

Prospective respiratory gating is normally more efficient than retrospective respiratory gating. A prerequisite for prospective respiratory gating is a real-time capability of the normally-provided control software for the MR apparatus.

For this purpose, real-time capability means that data measured with the sequence (in this case, the sequence comprises imaging and navigator sequences) can be evaluated during the sequencing, and the further course of the sequencing can be influenced by the results of this evaluation, wherein the time period between recording the data and influencing the further course is short in comparison with the typical time constants of the respiratory movement (in this case, particularly, the respiratory cycle of a human being, which amounts to between 3 and 10 seconds).

The main problem with the acceptance/rejection algorithm is that the respiration of the patient frequently varies during the examination. The variations in the respiratory movement can be, thereby, such that the respiratory positions within the once specified acceptance window are rarely, or no longer, detected. This leads to extended acquisition periods and can even lead to the measurement not being completed at all in the normal manner.

A large number of alternative prospective gating algorithms exist, which either attempt to improve the efficiency with respect to the acceptance/rejection algorithm, or to make the measurements more robust, for the case that the respiration during the measurement varies or drifts. Common to all of this is that—as long as the respiration is recorded with a navigator—the prospective decision is based solely on the last measured respiration position (e.g. the last measured diaphragm position or the last measured diaphragm positions).

The most important algorithm, by far, that addresses this problem is "Phase Ordering With Automatic Window Selection" (PAWS), which is described, for example, in the article by P. Jhooti, P. D. Gatehouse, J. Keegan, N. H. Bunce, A. M. Taylor, and D. N. Firmin, "Phase Ordering With Automatic Window Selection (PAWS): A Novel Motion-Resistant Technique for 3D Coronary Imaging," Magnetic Resonance in Medicine 43, Pages 470-480 (2000) and in the U.S. Pat. No. 7,039,451 B1. PAWS finds a final acceptance window during the runtime, and can thus react in a flexible manner to a changing respiration. A further goal of PAWS is to ensure a certain degree of "phase-encode ordering" (or in short, "phase ordering"). This means that adjacent lines in the k-space are acquired in similar respiration states. In particular, a variation in the respiratory state during acquisitions in the vicinity of the k-space center, which is particularly sensitive to movement, is to be avoided. PAWS was developed for a 3D Cartesian acquisition technique. The ky-kz array system used for this acquires a complete kx-kz plane of the 3-dimensional k-space following each navigator. The modulation of the k-space signal along the kz axis resulting from the transcendental state after interrupting the stationary steady state by the navigator (as well as potential activated preparation pulses, or the waiting for a further physiological signal, such as an EKG trigger) on the kx-kz plane, is therefore smooth. Discontinuations may arise in the ky axis as a result of residual movement, which can be manifested in the image as artifacts and blurring along the first phase encoding axis ky. This does not only apply when the segment border exists in the vicinity of the k-space center. Peristaltic movements, as well, which are not detected by the respiratory sensor, can lead to artifacts in the images.

PAWS exists in different so-called "bin" variations. In PAWS, the width of the final acceptance window is determined. The respiratory positions encompassed by this acceptance window are found automatically during the runtime, in contrast to acceptance/rejection algorithms. The filling of k-space occurs in clusters. A cluster (in the original work, the term "bin" is used instead of "cluster") is characterized by a respiratory position range, an acceptance range, and comprises all k-space lines that have already been measured, after which a respiratory position in the respiratory position range assigned to the cluster is measured. In the n-bin variation of PAWS a respiratory position range is covered by n successive clusters, the width of which range is the same as the acceptance window.

Furthermore, a starting position in the k-space is assigned to each cluster, wherein the number of different starting positions is n. Different starting positions are assigned to clusters with adjacent respiratory positions where n>1. As soon as a respiratory position assigned to a cluster is measured with the navigator, the measurement of a k-space line that has not yet been measured within said cluster is initiated. The decision regarding which k-space lines still to be measured are selected takes into consideration, as a whole, the already acquired k-space lines of adjacent clusters as well. By way of example, a still missing k-space line is selected such that an arbitrary group of n adjacent clusters is complete to the greatest degree possible, wherein the arbitrary group of n adjacent clusters contains the cluster to which the current measured respiratory position is assigned; i.e. the group of n adjacent clusters comprising the largest possible number of different k-space lines. As soon as an arbitrary group of n adjacent clusters comprises all of the k-space lines that are to be measured, the measurement is stopped, because the overall variation in the respiratory position is limited in these measurement data, thereby, to the acceptance window.

The n different starting points and clusters of the n-bin variation of PAWS normally result in n segments in the k-space. For this, each segment consists of adjacent k-space lines. The variations to the respiratory positions within a segment measured with the navigator correspond to the position range assigned to a cluster (in the original work, the term "bin size" is used), and thus one $n^{th}$ of the acquisition window. The variation to the respiratory position is greater over the course of the entire k-space, and has an upper limit as a result of the specified acceptance window. The lines belonging to the same segment are measured during similar respiratory states. Thus, the modulation of the signal changes with the respiration at the segment borders. As a result, position jumps occur at the segment borders. An aim of the different bin-variations of PAWS is to displace the segment borders away from the movement sensitive k-space center. Another aim is to obtain a greater degree of efficiency.

In the previously mentioned article by Jhooti et al., as well as in the follow-up work by P. Jhooti, P. Gatehouse J. Keegan, A. Stemmer, D. Firmin: "Phase ordering with Automatic Window Selection (PAWS) with Half Fourier for Increased Scan Efficiency and Image Quality;" Proc. Intl. Soc. Mag. Reson. Med. 11 (2004); Page 2146, the 1-bin, 2-bin, 3-bin, and 4-bin variations are compared with one another. The result of this comparison shows that the 1-bin and the 2-bin variations of PAWS are the most efficient, i.e. for a given width of the acceptance window, the measurements are completed most quickly. The 1-bin variation is discarded because it does not allow for "phase ordering," the 4-bin variation (and higher) is discarded due to lower efficiency. The 3-bin variation is less efficient than the 2-bin variation. The reason for this is the unidirectional growth direction of the cluster with starting positions at the left and right k-space edges. As soon as the gap between one of these peripheral clusters and the central cluster (with a starting position in the k-space center, and a bidirectional growth direction) is closed, then said clusters continue to grow until the gap between the other peripheral clusters and the central cluster is closed, as soon as a respiratory position is measured that is assigned to the first peripheral cluster. This normally leads to multiple k-space lines acquired at the cluster borders (segment borders). This problem does not exist with the 2-bin variation. In this variation, every second cluster grows in a unidirectional manner from the left-hand k-space edge, through the k-space center, toward the right-hand k-space edge, and the remaining clusters grow in a unidirectional manner from the right-hand k-space edge, through the k-space center, toward the left-hand k-space edge. The measurement is complete as soon as two adjacent clusters (with opposite growth directions) "meet." However, with a symmetrical scanning of the k-space, as is the case with the 2-bin variation, the cluster border frequently lies in the vicinity of the k-space center, which is particularly sensitive to movement, which may lead to strong image artifacts. The probability of cluster borders lying in the vicinity of the k-space center is substantially lower with the use of partial Fourier (i.e. an asymmetric scanning of the k-space).

Of practical relevance, therefore, are the so-called 2-bin and 3-bin versions of PAWS, wherein, with symmetrical scanning, the 3-bin variation is preferred, and with asymmetric scanning, the 2-bin variation is preferred. This analysis is based on a 2-bin variation, in which the starting position alternates between the left-hand and right-hand k-space edges of adjacent clusters. Accordingly, the clusters grow, respectively, from the starting positions assigned thereto, firstly toward the k-space center.

It should also be noted that in some works, only a single respiratory position is assigned to a cluster. The width of the final acceptance window then amounts to n times the resolution of the respiratory signal. In this alternative formulation, one obtains a flexible selection of the acceptance window in that one first enlarges the respiratory position measured with the sensor, such that the n adjacent resulting respiratory positions cover a respiratory range corresponding to the width of the acceptance window.

PAWS was originally developed for a ky-kz array system, with which, in each case after recording the respiratory signal, all k-space lines are acquired with a specific value of the second phase-encoding gradient (in the kz axis). Accordingly, the "phase-ordering" is also limited to a Cartesian k-space axis, which can lead to a higher occurrence of residual movement artifacts in this axis.

Another prospective gating algorithm, which addresses the problem of a varying respiration, is the Diminishing Variance Algorithm (DVA) (Todd S. Sachs, Craig H. Meyer, Pablo Irarrazabal, Bob S. Hu, Dwight G. Nishimura: "The Diminishing Variance Algorithm for Real-Time Reduction of Motion Artifacts in MRI;" MRM 34; Pages 412-422 (1995)). First, in an initial phase, the k-space that is to be acquired is completely recorded, without gating, and for each acquisition period, the displacement of the respiration position in relation to a reference position is measured with a navigator, and recorded. At the end of the initial phase, the most frequent respiratory position is determined using a histogram, and designated as the mode for the statistical distribution. The k-space data, the stored respiratory positions of which deviate the most from the mode, are then re-acquired together with the navigator, and the histogram (and thereby the mode) is updated. This re-acquisition of the k-space data, which in each case deviate the most from the current mode, is continued until all of the respiratory positions lie within an acceptance window of a given width, or a time limit has been reached.

SUMMARY OF THE INVENTION

An object of the invention is to provide a method, a magnetic resonance apparatus, and a computer-readable data storage medium with which a respiratory phase can be determined from an ongoing measurement of a respiratory position.

Based on the observation that it makes a significant difference whether a specific navigator measurement is measured during the inhalation or during the exhalation, a desire has arisen for an algorithm, which enables the determination of the momentary respiratory phase, even if the scanning rate of the physiological respiratory movement is low, and each individual scanning point is encumbered by noise.

The reason that the respiratory phase, i.e. the phase of the respiratory cycle (inhalation or exhalation), has not yet been used with prospective respiratory gating with navigators, is presumably of a technical nature. The time interval between successive navigator measurements is relatively long, because each navigator measurement reduces, on the one hand, the efficiency of the measurement, and on the other hand, interrupts the dynamic equilibrium ("steady state") of the magnetization. At the same time, each navigator measurement is encumbered with noise, such that solely from the comparison of two successive navigator measurements, it is normally not possible to establish the momentary respiratory phase. This noise can be reduced by temporary means, or digital filters applied to the series of measured respiratory positions. Both delay, however, the availability of the information, and can thus render the making of a prospective decision impossible.

A method according to the invention for determining a respiratory phase from a series of measurements of a respiratory position determines the respiratory phase by means of a finite state machine, which processes a current measured respiratory position and at least one previously measured respiratory position, and assigns a current respiratory phase to the current respiratory position. For this, the temporal spacing of two successive measurements of the respiratory position is relatively small in relation to a respiratory cycle.

According to the invention, a method for determining a respiratory phase of a respiratory movement from a series of measurements of respiratory positions is made available, wherein the respiratory phase can contain numerous status values. For this, a current measured respiratory position and at least one previously measured respiratory position are processed, and a current status value of the respiratory phase is assigned to the current respiratory position, wherein the temporal spacing of two successive measurements of respiratory movements is relatively small compared to a respiratory cycle. A current respiratory position is measured, and a momentary status value of the respiratory phase is retrieved, which has been determined in the previous measurement of the respiratory position. Furthermore, a momentary valid maximum respiratory position as of the last change to the momentary status value of the respiratory phase, and/or a momentary valid minimum respiratory position lying below the previously determined respiratory positions, is determined. The current measured respiratory position is then compared with a previously determined maximum respiratory position and/or a previously determined minimum respiratory position, contingent on the momentary status value of the respiratory phase. In conclusion, a current status value of the respiratory phase can be determined, and a current maximum respiratory position as of the last change to the current respiratory phase, and/or a current minimum respiratory position as of the last change to the current respiratory phase, can be determined, contingent on the results of the comparison and the current respiratory position.

The method enables, with a determined respiratory phase, a continuous measurement of imaging measurement data to be influenced in a prospective manner. By this means, using the present invention, the most important prospective gating algorithm can be expanded in this respect, such that the decision, of whether a determined measurement point that needs to be referenced for the image reconstruction is a function of the respiratory position (e.g. diaphragm position) and the respiratory phase, can be made while the respiratory position is being measured. The respiratory phase is a binary status (inhalation, exhalation), or a triplet (inhalation, exhalation, unknown). By taking into consideration, in accordance with the invention, not only the respiratory position, but also the respiratory phase for which a individual measurement is acquired, it is possible to significantly reduce the actual overall variation to the respiratory position in the final measurement data set, in contrast to methods which only take the respiratory position into account.

The respiratory positions, and therefore the respiratory phases, can be determined for this, in particular, by means of navigator measurements. In some embodiments a determination of the respiratory positions and the respiratory phases is also possible by means of external sensors, such as, e.g. respiratory belts. The determination of the respiratory positions and the respiratory phases by means of navigators eliminates, however, the need for otherwise necessary additional external sensors, and the use thereof.

The respiratory phase can be assigned the values "inhalation" or "exhalation," in order to establish whether a patient to be examined is currently inhaling or exhaling during the acquisition of the measurement data. If neither of the two values "inhalation" or "exhalation" can be assigned, the respiratory phase can be assigned the value "unknown." Measurement data acquired during an "unknown" respiratory phase can be discarded. The respiratory phase can be determined, in particular, by at least two measurements of the respiratory position, wherein the temporal spacing between the two successive measurements of the respiratory position is relatively small with respect to a respiratory cycle. By way of example, the temporal spacing between two successive measurements of the respiratory position has a magnitude of ca. one eighth of the respiratory cycle or less.

A magnetic resonance apparatus according to the invention has a base field magnet, a gradient field system, a radio-frequency antenna, and a control device for controlling the gradient field system and the radio-frequency antenna, and an image processor for receiving measurement signals recorded by the radio-frequency antenna, for evaluating the measurement signals and for the creation of magnetic resonance images, and is designed or configured to execute the described method.

A non-transitory computer-readable data storage medium according to the invention has control data that can be read electronically stored thereon, which are designed to cause the described method to be executed a control device of a magnetic resonance apparatus into which the storage medium is loaded.

The advantages of the method, and the embodiments thereof, apply analogously to the magnetic resonance apparatus, and the data storage medium.

DESCRIPTION OF THE PREFERRED EMBODIMENTS

Figure 1:
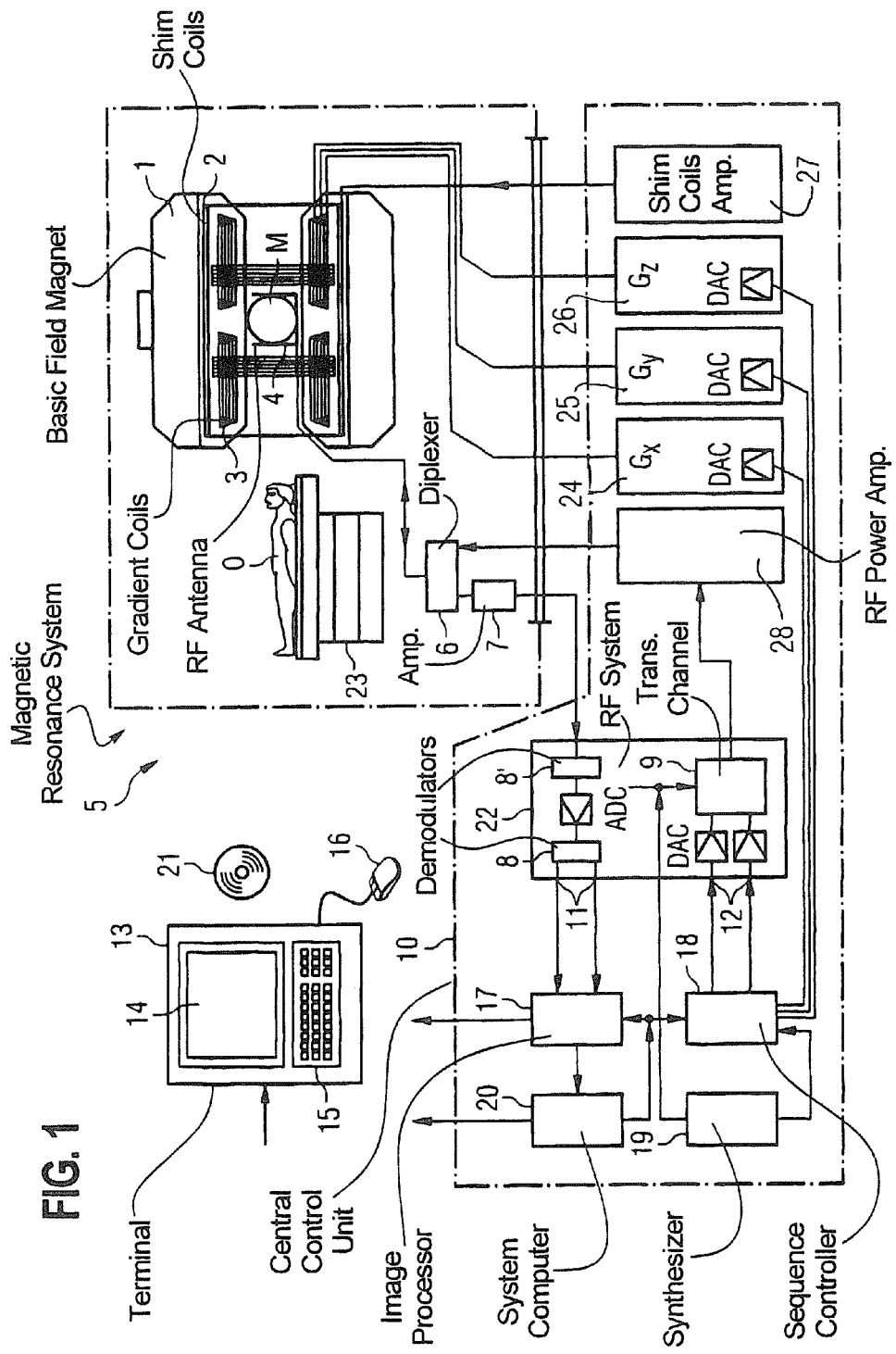
FIG. 1 schematically illustrates a magnetic resonance apparatus according to the invention.

FIG. 1 schematically illustrates a magnetic resonance apparatus 5 (a magnetic resonance imaging or tomography device). A basic field magnet 1 generates, a temporally constant strong magnetic field for the polarization or alignment of the nuclear spin in a region of an examination subject O , such as a portion of a human body that is to be examined, lying on a table 23 in order to be moved into the magnetic resonance apparatus 5. The high degree of homogeneity in the basic magnetic field necessary for the magnetic resonance measurement (data acquisition) is defined in a typically sphere-shaped measurement volume M, in which the portion of the human body that is to be examined is placed. In order to support the homogeneity requirements temporally constant effects are eliminated by shim-plates made of ferromagnetic materials are placed at appropriate positions. Temporally variable effects are eliminated by shim-coils 2 and an appropriate control unit 27 for the shim-coils 2.

A cylindrically shaped gradient coil system 3 is incorporated in the basic field magnets 1, composed of three windings. Each winding is supplied by a corresponding amplifier 24-26 with power for generating a linear gradient field in a respective axis of a Cartesian coordinate system. The first partial winding of the gradient field system 3 generates a gradient $G_x$ in the x-axis, the second partial winding generates a gradient $G_y$ in the y-axis, and the third partial winding generates a gradient $G_z$ in the z-axis. Each amplifier 24-26 has a digital-analog converter (DAC), controlled by a sequencer 18 for the accurately-times generation of gradient pulses.

A radio-frequency antenna 4 is located within the gradient field system 3, which converts the radio-frequency pulses provided by a radio-frequency power amplifier into a magnetic alternating field for the excitation of the nucleii by tipping ("flipping") the spins in the subject or the region thereof to be examined, from the alignment produced by the basic magnetic field. The radio-frequency antenna 4 is composed of one or more RF transmitting coils and one or more RF receiving coils in the form of an annular, linear or matrix type configuration of coils. The alternating field based on the precessing nuclear spin, i.e. the nuclear spin echo signal normally produced from a pulse sequence composed of one or more radio-frequency pulses and one or more gradient pulses, is also converted by the RF receiving coils of the radio-frequency antenna 4 into a voltage (measurement signal), which is transmitted to a radio-frequency system 22 via an amplifier 7 of a radio-frequency receiver channel 8, 8'. The radio-frequency system 22 furthermore has a transmitting channel 9, in which the radio-frequency pulses for the excitation of the magnetic nuclear resonance are generated. For this purpose, the respective radio-frequency pulses are digitally depicted in the sequencer 18 as a series of complex numbers, based on a given pulse sequence provided by the system computer 20. This number series is sent via an input 12, in each case, as real and imaginary number components to a digital-analog converter (DAC) in the radio-frequency system 22 and from there to the transmitting channel 9. The pulse sequences are modulated in the transmitting channel 9 to a radio-frequency carrier signal, the base frequency of which corresponds to the resonance frequency of the nuclear spin in the measurement volume. The modulated pulse sequences of the RF transmitter coil are transmitted to the radio-frequency antenna 4 via an amplifier 28.

Switching from transmitting to receiving operation occurs via a transmission-receiving switch 6. The RF transmitting coil of the radio-frequency antenna 4 radiates the radio-frequency pulse for the excitation of the nuclear spin in the measurement volume M and scans the resulting echo signals via the RF receiving coils. The corresponding magnetic resonance signals obtained thereby are demodulated to an intermediate frequency in a phase sensitive manner in a first demodulator 8' of the receiving channel of the radio-frequency system 22, and digitalized in an analog-digital converter (ADC). This signal is then demodulated to the base frequency. The demodulation to the base frequency and the separation into real and imaginary parts occurs after digitization in the spatial domain in a second demodulator 8, which emits the demodulated data via outputs 11 to an image processor 17. In an image processor 17, an MR image is reconstructed from the measurement data obtained in this manner through the use of the method according to the invention, that includes computation of at least one disturbance matrix and the inversion thereof, in the image processor 17. The management of the measurement data, the image data, and the control program occurs via the system computer 20. The sequencer 18 controls the generation of the desired pulse sequences and the corresponding scanning of k-space with control programs, in particular, in accordance with the method according to the invention. The sequencer 18 controls accurately-timed switching (activation) of the gradients, the transmission of the radio-frequency pulse with a defined phase amplitude, and the reception of the magnetic resonance signals. The time base for the radio-frequency system 22 and the sequencer 18 is provided by a synthesizer 19. The selection of appropriate control programs for the generation of an MR image, which are stored, for example, on a DVD 21, as well as other user inputs such as a desired number n of adjacent clusters, which are to collectively cover the desired k-space, and the display of the generated MR images, occurs via a terminal 13, which includes units for enabling input entries, such as, e.g. a keyboard 15, and/or a mouse 16, and a unit for enabling a display, such as, e.g. a display screen.

Figure 2:
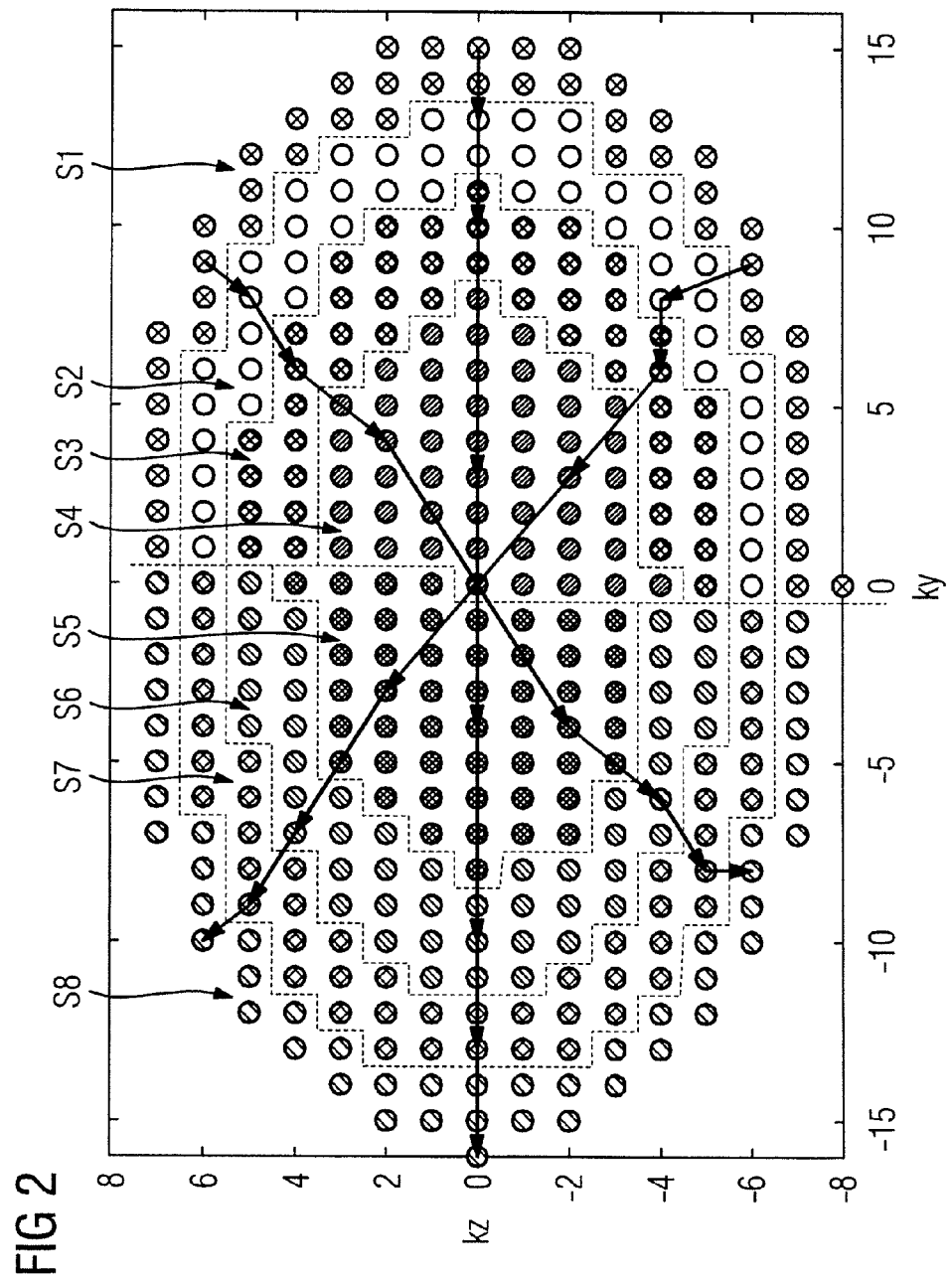
FIG. 2 shows an example of a new allocation of views to sectors and shots.

FIG. 2 shows an example of a new k-space array system. A kz-ky plane is shown, in which views (depicted by circles filled with various patterns) are disposed in a Cartesian manner.

Figure 3:
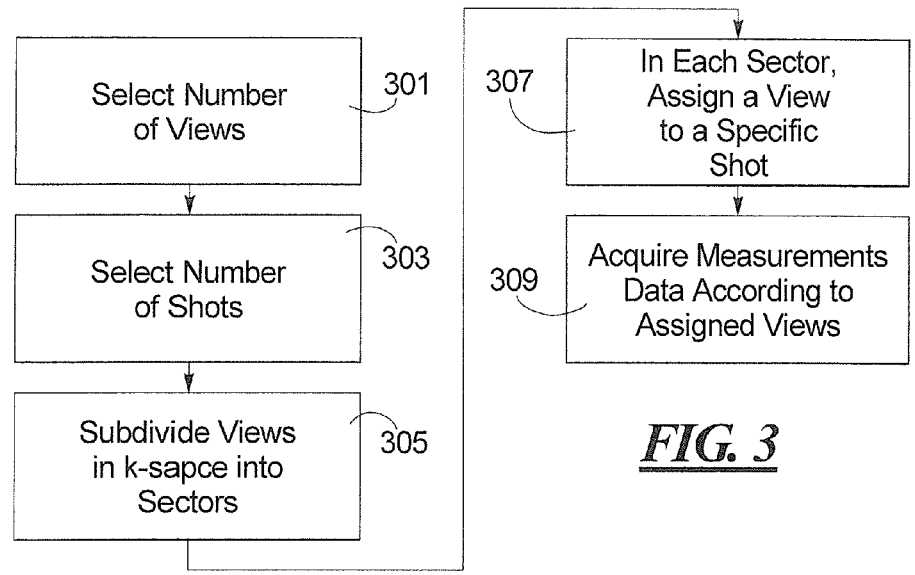
FIG. 3 is a flow chart for a new array of k-space to be scanned in sectors and shots.

FIG. 3 shows a flow chart for arranging the k-space that is to be scanned in sectors and shots.

For this purpose, first a number Nv of views, which are to be acquired for each shot, is selected (block 301 ). This occurs, for example, by means of an input by a user at a terminal 13 of a magnetic resonance apparatus 5. The selection of the views per shot can be freely selected with, for example, the use of a navigator for determining the respiratory signal as a physiological signal, as well as the temporal resolution of the respiratory signal, because after a navigator, a shot with the selected number of views is acquired. From the total number of the views to be measured, (which is determined by means of, among other factors, the resolution, which has, in turn, been selected by the user) and the number Nv of views per shot is therefore established by the number Ns of shots which are required in order to fully scan the k-space that is to be scanned (block 303).

The views in the k-space are subdivided into sectors S1, S2, S3, S4, S5, S6, S7, S8 (block 305). Views which are assigned to the same sector are each filled with the same pattern. In addition, the borders of the sectors S1, S2, S3, S4, S5, S6, S7, S8 are indicated by thin broken lines.

The number of different sectors is the same as the number of views per shot, and, e.g. a user-defined parameter. In the depicted example, the number of sectors and the views per shot equals eight.

The number of views per sector is the same as the number of shots Ns. In the example, the number of views in each sector, and therefore the number of shots, equals 49. Views which are assigned to the same sector have a similar spacing from the k-space center, and are located in the same hemisphere (in the example in FIG. 2, the first hemisphere is defined by ky>0, or (ky=0 and kz≤0)). Advantages derived therefrom are obtained with an asymmetric recording of the k-space (partial Fourier).

Each shot acquires, thus, one view per sector. For this, views of a specific sector are acquired at the same point in time after the navigator sequence, or after the starting of the shots, respectively.

All views are assigned to a shot, wherein in each sector a view is assigned to a specific shot (block 307). The assignment of the individual views of a sector to a specific shot occurs in accordance with their orientation in the kz-ky plane, for example, in accordance with their azimuth angle in a polar coordinate system. This array results in a smooth modulation of the k-space (resulting from the transcendental state after an interruption of the stationary steady state) along the quasi-radial scanning direction.

As an example, three shots are depicted in FIG. 2 by means of thick series of arrows. With the acquisition of measurement data, the views assigned to the same sector and to different shots each assume the same position within the shots (block 309). As one sees in the example in FIG. 2, the sequence for the acquired views for each shot corresponds respectively to the sectors thereof, which, in the depicted case, are from S1 to S2 to S3 to S4 to S5 to S6 to S7 to S8. The shots thus proceed in quasi-radial k-space trajectories, in this case from the right edge to the left edge of the k-space that is to be scanned.

The array system has the advantage, in comparison with the array system previously used in conjunction with the PAWS technique, that it is less susceptible to ghost artifacts resulting from residual movement, because these are smeared at the azimuth. Furthermore, the array allows for a free selection of the views per shot, and therefore the temporal resolution of the physiological respiratory signal recorded with the navigator sequence. Furthermore, it is compatible with so-called elliptical scanning, in which the views in the peripheral corners of the k-space, particularly in the ky-kz plane, having a relatively low information content, are not acquired, in favor of a shorter measurement time period, as is also the case in the depicted example. Furthermore, the intended distribution of the k-space sectors is compatible with a varying density of the k-space scanning, as is the case, for example, with parallel imaging with auto-calibration.

The generalized PAWS description enables the array system described above to be implemented together with PAWS, in that the shots, as already mentioned above, are assigned a shot index for the views distributed in the sectors, which fulfills the suppositions c) and d) given above.

For this, the following approach can be used:

First, each shot exhibits an azimuth angle $\phi$ e.g. between $[-\pi, \pi]$. For this, one can, e.g., use the average azimuth angle of the views per shot (arctan 2 (ky, kz)) in the first hemisphere, or the azimuth angle of the views in one of the sectors, advantageously one of the sectors lying in the vicinity of the k-space center, such as the sector S4 in FIG. 2. This azimuth angle is a suitable scalar, and therefore array criteria, for the shots, which describes a neighborhood of the shots. It is important that one realizes that it is not necessary for the allocation shot→scalar to be reversible. The shot index ns0 is set advantageously to be equal to the shot index of the shots acquiring the k-space center. In the example in FIG. 2, this shot has an azimuth angle φ=0, and thus lies in the center of the evaluation range of ns [0, Ns−1].

In a truly radial trajectory, all shots have the same degree of sensitivity to movement. Nevertheless, one can still use the generalized PAWS description. The selection of the ns0 is then free.

Figure 5:
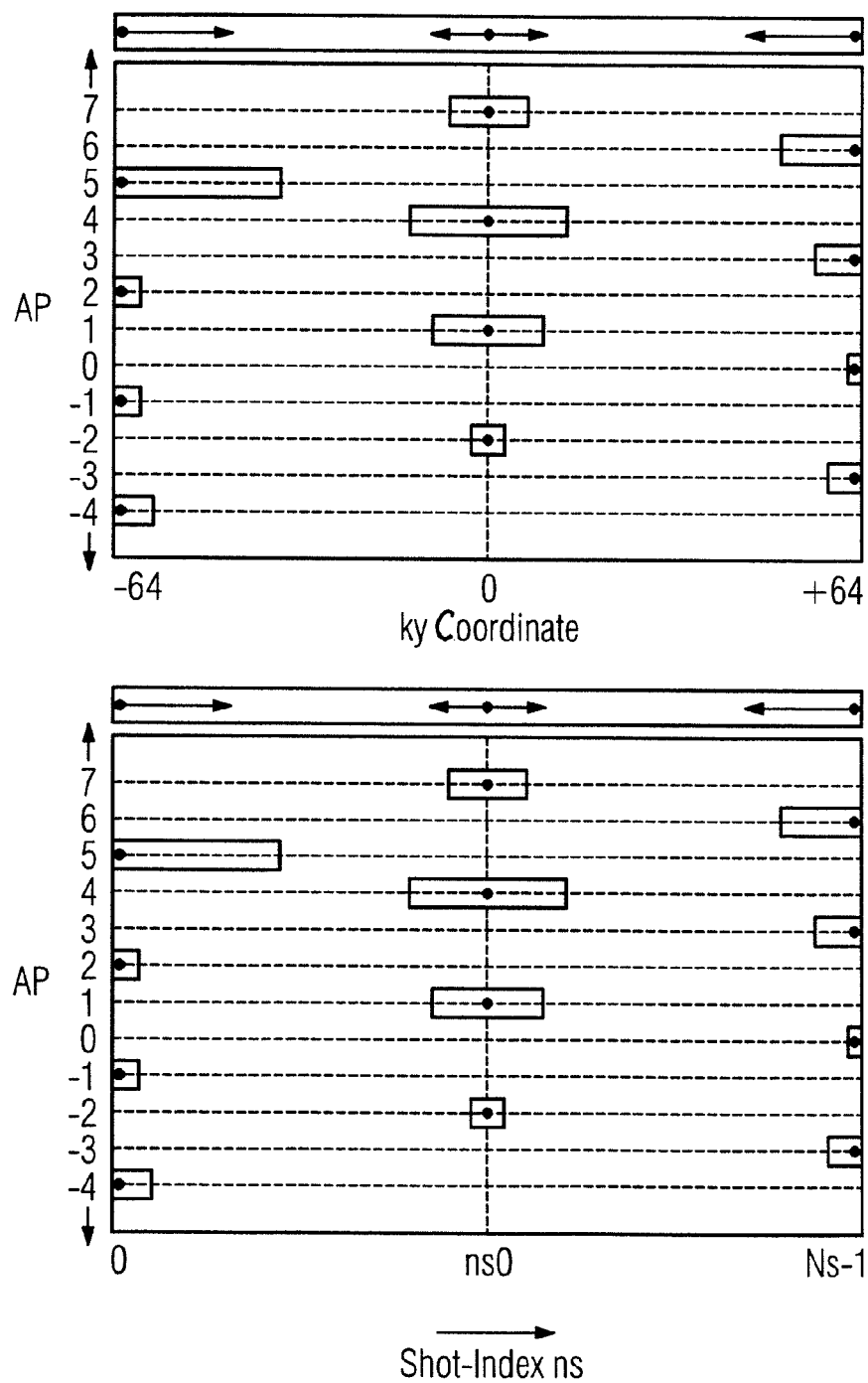
FIG. 5 shows an example of a comparison of the PAWS array system of the original work using on the ky-coordinate with a new array system according to the shot index for a 3-bin PAWS algorithm.

With the determination by means of the above suppositions a)-d), one can thus use the PAWS algorithm on arbitrary 2-dimensional Cartesian ky-kz array systems and k-space trajectories, in that one replaces the ky coordinates of the original work (Jhooti et al.) with the shot index ns. This is simply done, in that a cluster ("bin" in the original work) is assigned a starting position at the left-hand k-space edge (kymin in the original work) of the shot index ns=0 as the starting position, and a cluster with a starting position on the right-hand k-space edge (kymax in the original work) is assigned the shot index ns=Ns−1 as the starting position, and a cluster having the starting position in the k-space center (in the original work) is assigned the shot index ns=ns0, with a maximum movement sensitivity, as the starting position. In FIG. 5, an example of a transformation of this type is depicted, from the array system of the original work using the ky coordinate (above) to an array system in accordance with the shot index for a 3-bin PAWS algorithm (below). In the vertical column, the respiratory position AP is recorded for each case.

Figure 4:
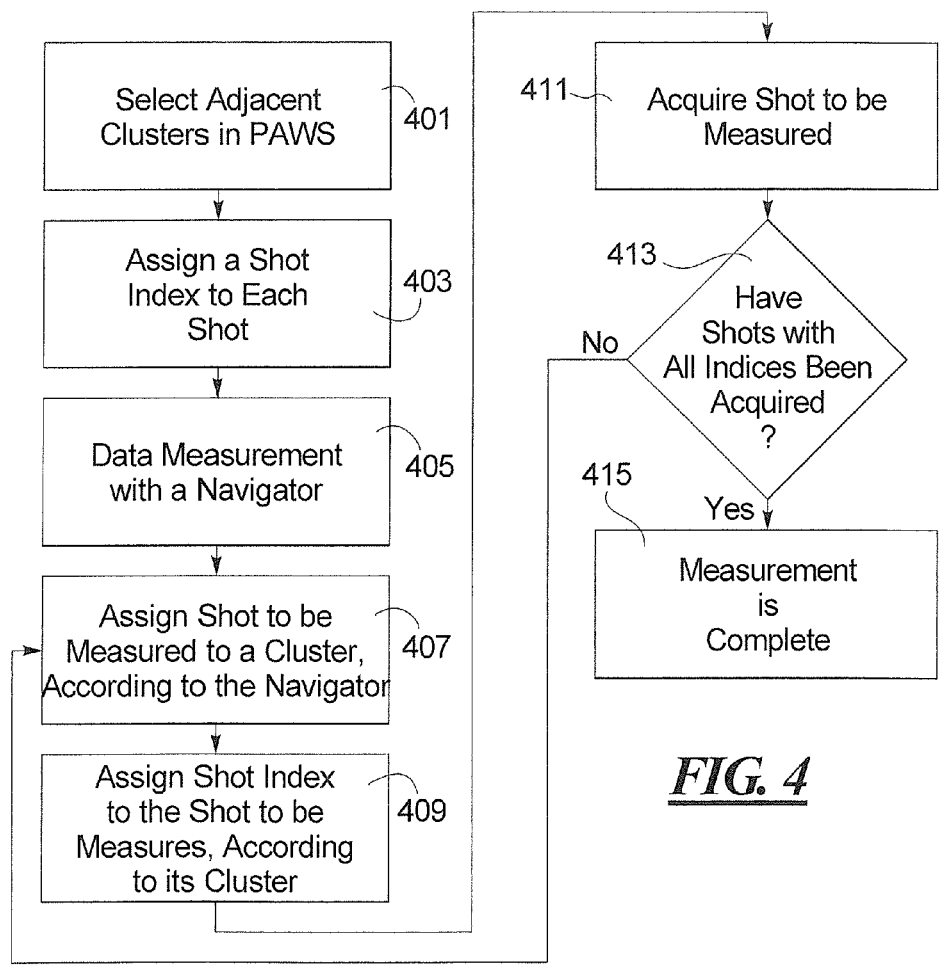
FIG. 4 is a flow chart of a new PAWS method.

A flow chart for a generalized PAWS method is depicted in FIG. 4.

For this, first, as is normal with PAWS, the number n is selected, which indicates the number of adjacent clusters that should, collectively, completely fill the k-space, in order to obtain a complete measurement data set, which does not exceed a given overall variation to the respiratory position during the measurements (block 401).

Each of the Ns shots is assigned a shot index ns∈[0; ... ; ns0; ... ; Ns−1] (block 403), as described above, wherein the assignment occurs such that the shot indices ns are arranged such that the sensitivity of the shots with respect to movement by the examination subject increases from shot index ns=0 up to shot index ns=ns0, and in turn, decreases from shot index ns=ns0 to shot index ns=Ns−1.

The measurement is initiated with a navigator measurement for determining a respiratory signal and therefore a momentary respiratory position (block 405).

For this purpose, the shot that is to be measured after the navigator measurement is assigned to a cluster, in the PAWS method, in a typical manner, corresponding to the respiratory signal measured with the navigator measurement (block 407).

After it has been determined by the navigator measurement, to which cluster the following shot that is to be measured is assigned, a shot index is determined for the shot to be measured, in relation to the already acquired shot indices for the previously selected cluster and its adjacent clusters (block 409). If no shot has yet been acquired in the cluster to which the measured shot is to be assigned, the shot having the shot index corresponding to the starting position assigned to said cluster is selected (block 409).

The corresponding shot with the selected shot index is acquired as the shot that is to be measured (block 411).

If, after the last acquisition of a shot, in a given number n of adjacent clusters, all of the shots with all of the Ns shot indices have been acquired (query 413) then the measurement is complete (block 415).

Accordingly, with the generalized PAWS method as well, a so-called peripheral cluster having a starting position 0 grows toward the k-space center, in that it selects the next, not yet acquired, larger shot index, and a peripheral cluster having a starting position Ns−1 grows in that it selects the next smaller, not yet acquired shot index.

The central cluster (having the starting position ns0) selects from the n possible cluster combinations the cluster that is complete to the greatest extent, i.e. the cluster already comprising the most shots having different shot indices, and then grows toward a smaller, or larger, respectively, shot index, depending on whether the quantity formed by shots having ns ≤ ns0, or, respectively, the quantity formed by shots having ns ≥ ns0, which are not yet acquired from the cluster combination, has more elements. As soon as an arbitrary group of n adjacent clusters comprises all of the shot indices [0, ... , Ns−1] that are to be measured, the measurement is complete (block 415), because the overall variation in the respiratory position is thus limited to the acceptance window. If there are still cluster combinations of n adjacent clusters shots in which not all Ns shot indices are comprised, then at block 407, the method is continued, and a new navigator measurement is acquired, in each case, with a new subsequent shot.

In the example in FIG. 2, adjacent views in the k-space each belong to shots with a similar azimuth angle, and thus to shots with adjacent shot indices. By this means, the generalized PAWS algorithm ensures that adjacent views are acquired during similar respiratory states. In the example in FIG. 2, the shot that acquires the k-space center has the azimuth angle φ=0, and thus lies in the center of the evaluation range of the shot indices. One can thus assume that the results contained in the original work (with regard to efficiency and remaining susceptibility to movement) can also be directly applied to the proposed, more flexible, ky-kz array system. With the described method, the PAWS concept can be used with any arbitrary ky-kz array system and with any arbitrary non-Cartesian k-space trajectories.

With the use of a navigator for recording the movement, the stationary steady state of the magnetization is interrupted by the execution of the navigator sequence. With the array system according to the original work from Jhooti et al., this interruption occurs, in each case, after the acquisition of Nz TR intervals, wherein Nz is the number of phase encoding steps in the second phase encoding direction. The temporal resolution of the respiratory signal is thus linked directly to the spatial resolution of the imaging sequence along the second phase encoding direction. However, the respiratory signal measured with the navigator is only valid for a limited period of time, which is short in relation to the respiratory interval. This means that the array system used in the original work by Jhooti et al. inherently limits the maximum resolution in one of the two Cartesian axes. With the use of the proposed, generalized PAWS algorithm, having an array system such as that described, in particular, in reference to FIG. 2, a limitation of this type does not exist, because the number of views per shot, and thus the temporal resolution of the respiratory signal, can be freely selected. This advantage is particularly important, because the goal of respiratory gated measurements is frequently to avoid the inherent resolution limitation to measurements made while holding one's breath, resulting from the limited ability of the patient to hold its breath for longer periods of time.

The problem of the limited temporal validity of the navigator signal can be avoided in part through the use of a 1-dimensional centric array system along the kz axis. An array system of this type starts in the k-space center, and acquires alternating views with positive and negative values for kz, in such a manner that the absolute moment of the phase encoding steps grows in a continuous manner. This centric array system has, however, the disadvantage that it can lead to artifacts resulting from turbulences as a result of the larger phase encoding jumps between the TR intervals.

As an alternative to the normal n-bin PAWS method, in the following an optimized 2-bin PAWS method shall be presented.

Figure 6:
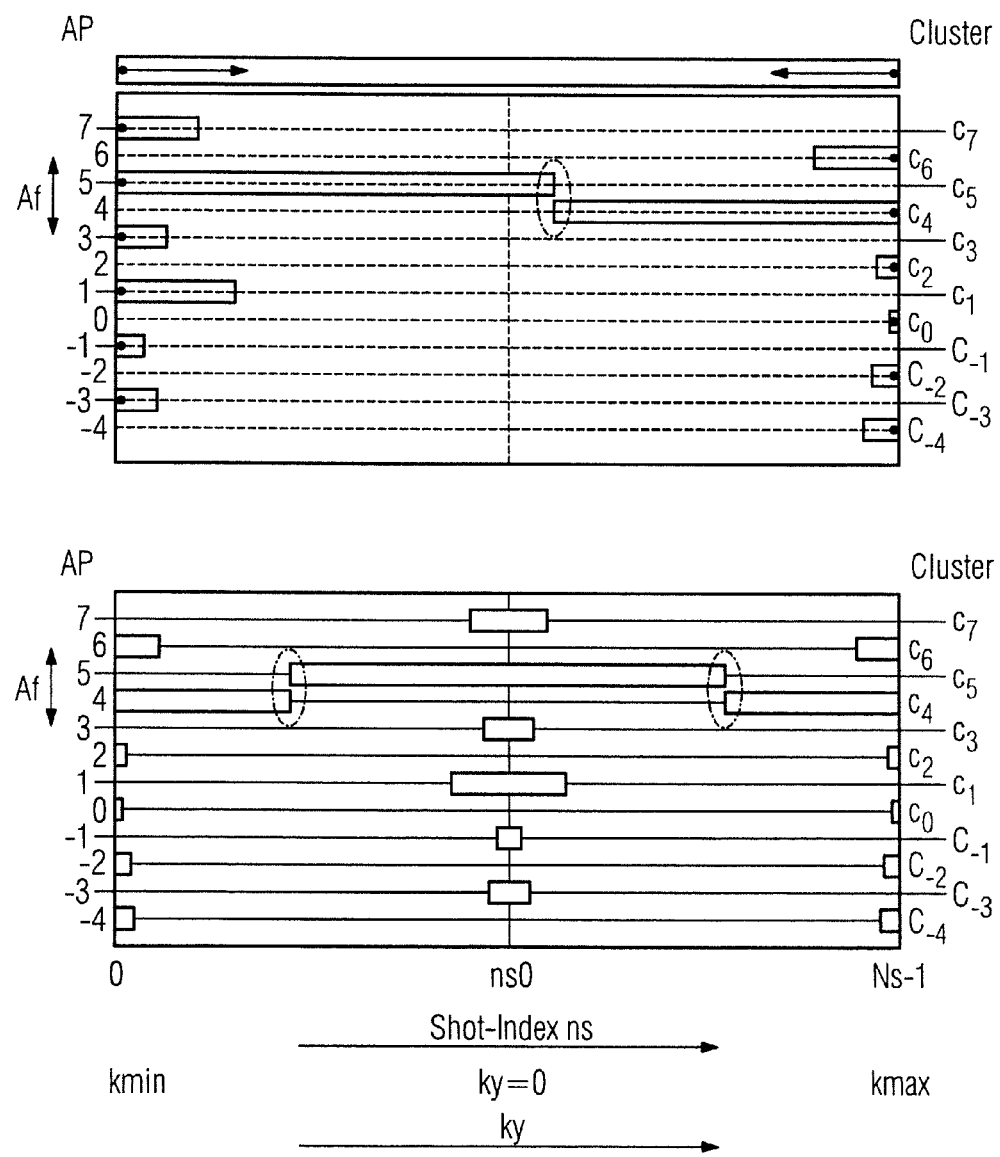
FIG. 6 shows an example of a comparison of the previous 2-bin PAWS with a new optimized 2-bin PAWS.

FIG. 6 shows, by way of example, a comparison of the previous 2-bin PAWS with a new, optimized 2-bin PAWS, wherein a prior 2-bin PAWS is depicted at the top, and the new 2-bin PAWS is depicted below.

As is described in the original work (Jhooti et al.), in the original 2-bin PAWS variation the starting position of adjacent clusters alternates between the left-hand and the right-hand k-space edge. In the upper part of FIG. 6, clusters having an even-numbered index are assigned the right-hand starting position, and clusters with an odd-numbered index are assigned the left-hand starting position. This corresponds in the generalized depiction, described herein, to an alternation between ns=0 and ns=Ns−1. Accordingly, a cluster with the starting position ns=0 grows, in that it selects the smallest shot index that has not yet been acquired from the cluster. A cluster with a starting position ns=Ns−1 grows in that it selects the largest shot index that has not yet been acquired from the cluster. In the following, a shot index ns shall always be referred to, even if the original array can be used in accordance with the ky coordinates. The width of the respiration position range assigned to each cluster normally corresponds to half of the acceptance window (AF). The measurement is complete as soon as two arbitrary adjacent clusters have collectively acquired all shots. This is the case in the example in FIG. 6 for the clusters c4 and c5. In terms of imaging, a cluster "growing from the left side" (starting position ns=0) and one of the two adjacent clusters "growing from the right side" (starting position ns=Ns−1) meet, such that both clusters, collectively, span the overall value range [0, . . . , Ns−1]. To the extent that these two clusters comprise nearly the same number of shots, frequently a cluster border (marked with an oval drawn with a broken line in FIG. 6.) is then obtained in this connection in the movement sensitive region surrounding the k-space center.

In the optimal 2-bin PAWS implementation presented here, two cluster types also alternate. The one cluster type has the shot having the maximum movement sensitivity ns=ns0 as the starting position and shall be referred to in the following as the central cluster. The other cluster type does not have a clear starting position, and shall be referred to in the following as a peripheral cluster. In the example in FIG. 6, clusters with an odd-numbered index are central clusters, and clusters with an even-numbered index are peripheral clusters. The starting position of a peripheral cluster is either ns=0, or ns=Ns−1, or, respectively, either the right-hand or the left-hand k-space edge in the ky coordinates, wherein the actual starting position is first decided on during the runtime. A peripheral cluster grows, independently of its starting position, either from the largest shot index not yet belonging to the cluster, downward toward ns0, or ky=0, respectively, or from the smallest shot index not yet belonging to the cluster, upward toward ns0 or, ky=0, respectively. The decision as to which direction of growth shall currently be preferred, occurs in turn during the runtime. This is schematically depicted in a flow chart in FIG. 7.

If, as has already been described above, a respiratory position is measured by means of a navigator measurement (block 701, corresponding to block 405 in FIG. 4), which lies in the respiratory position range of a peripheral cluster cn, in accordance with the normal array used in PAWS (block 407 in FIG. 4), then it is next queried whether the cluster combination cn−c(n−1) or cn−c(n+1) is closer to completion (blocks 705 and 707. For this purpose, the shots already acquired in the clusters cn−c(n−1) and cn−c(n+1) are first counted, and these are stored with the respective number M− or M+(block 705). The adjacent cluster cx, which, together with the peripheral cluster cn, is closest to completion, is selected according to these numbers M− or M+, wherein the cluster c(n−1) is selected if M+ is greater than M−. The clusters are labeled in the normal fashion, corresponding to their respiratory position range (cluster cn corresponds to the $n^{th}$ respiratory position). Accordingly, c(n−1) and c(n+1) are central clusters, and the next two neighbors thereof are peripheral clusters cn. In this manner, the cluster c(n−1) is selected if the cluster combination cn−c(n−1) is closer to completion, and otherwise, the cluster c(n+1) is selected.

Next, the number of shots Mlow, having an index in the range [0, ns], which have not yet been acquired from the two clusters (cn and the selected cx), and the number of shots Mhigh, having an index in the range [ns, . . . , Ns−1], which have not yet been acquired from the two clusters, are counted (block 709). If the cluster cn, which is assigned to the last measured respiratory position, as in the given case, is a peripheral cluster ("y" in query 711), then the peripheral cluster cn grows from its smallest not yet acquired shot index toward ns0, or ky=0, respectively, if Mlow is greater than Mhigh ("y" in query 713), in which the smallest, not yet acquired, shot index is acquired (block 715); otherwise, it grows from its largest not yet acquired shot index toward ns0, or ky=0, respectively ("n" in query 713), in which the largest, not yet acquired shot index, is acquired (block 715).

A peripheral cluster spans, therefore, in general, two contiguous index ranges. The one starts at the smallest shot index ns=0 (or the left-hand k-space edge), and grows toward larger shot indices. The other starts at the largest shot index ns=Ns−1 (or the right-hand k-space edge), and grows toward smaller shot indices. Alternatively, one can also refer to the index range for peripheral clusters being continued at the range borders in a periodic or cyclical manner.

The decision process runs in a similar manner, when the last measured respiratory position lies in the respiratory position range of a central cluster cn.

As explained above, it is checked to see which of the cluster combinations, cn−c(n−1) and cn−c(n+1), is closer to completion, and this cluster combination is selected (blocks 705 and 707). Next, the number of shots Mlow, having an index in the range [0, ns], which are not yet acquired from the two clusters, as well as the number of shots Mhigh, having an index in the range [ns, . . . , Ns−1], which are not yet acquired from the two clusters, are counted (block 709). If the cluster cn, which is assigned to the last measured respiratory position, is a central, as is assumed in the present case, ("n" in query 711), then the central cluster cn, if Mlow is greater than Mhigh, grows from its smallest already acquired shot index toward ns=0, or kmin, respectively ("n" in query 719), in which the largest of the not yet acquired shot indices is acquired, which is smaller than the smallest already acquired shot index (block 723). Otherwise (Mhigh is greater than Mlow) ("y" in query 719) the cluster cn grows from its largest already acquired shot index toward Ns−1, or kmax, respectively, in which the smallest of the shot indices that is larger than the largest already acquired shot index is acquired (block 721).

In any case, after an acquisition of a shot in one of the blocks 715, 717, 721 and 723, it is checked in query 725 whether all Ns desired shot indices are already acquired in the selected cluster combination. If this is the case ("y" in query 725), the measurement is complete (block 727), and can be stopped; if not ("n" in query 725), then the process is continued with a new navigator measurement. In this manner, the termination criteria remains unchanged with respect to the original version of PAWS; as soon as an arbitrary group of two adjacent clusters (2-bin) has acquired all of the shot indices that are to be measured, the measurement is terminated, because the overall variation of the respiratory position is limited thereby to the acceptance window.

Figure 7:
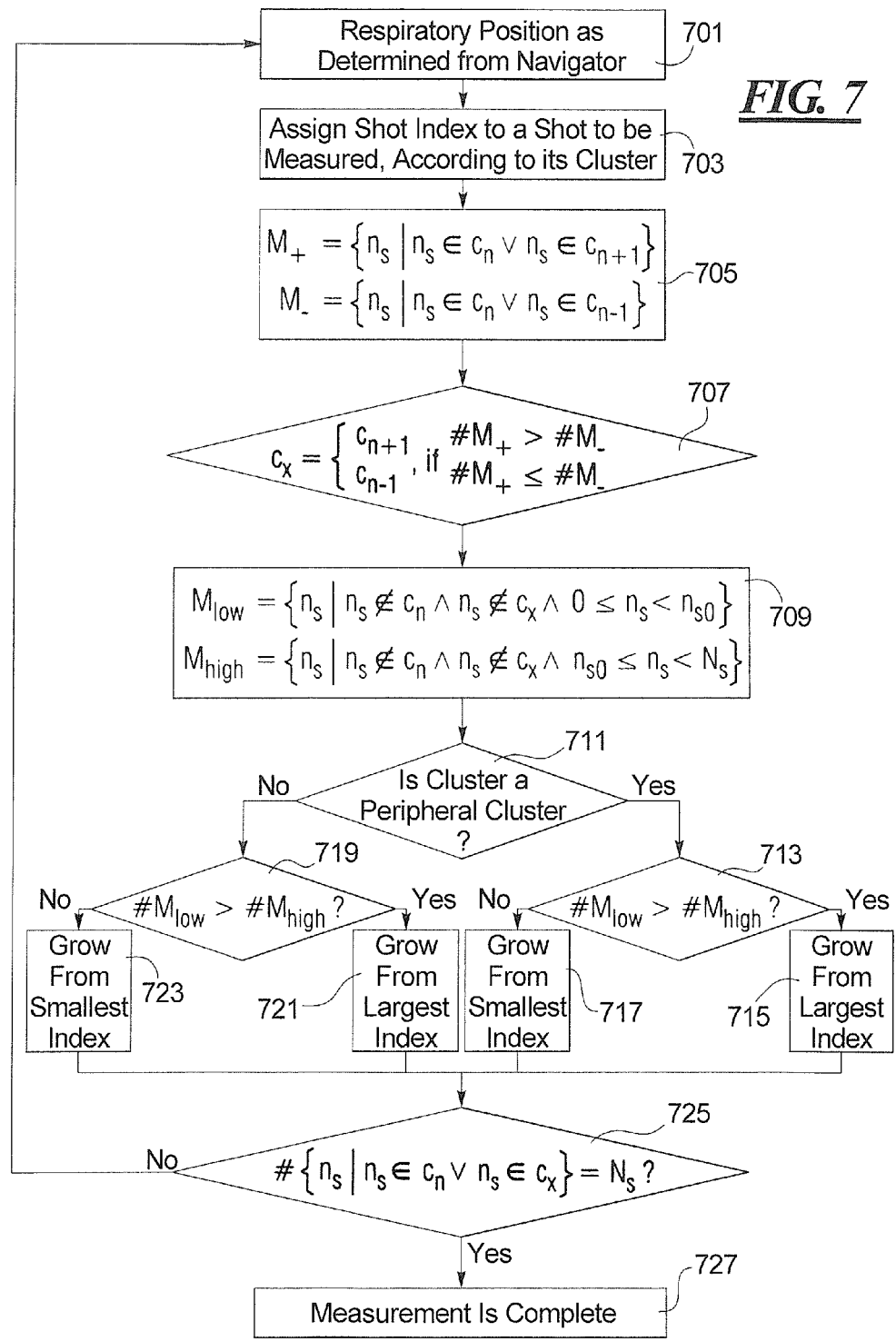
FIG. 7 is a flow chart for the optimized 2-bin PAWS.

In the flowchart in FIG. 7, which summarizes the algorithm described above, the usual symbols of set theory are used:

{.} ... means a quantity.
{xs| ... } ... means the set of all indices shot xs "... applies to ... "
∈ ... means "is an element of".
{.} ... denotes the number of elements of the set.
∧ ... logical symbol for "and".
∨ ... logical symbol for "or".

This optimal 2-bin version of PAWS unites the high degree of efficiency of the original 2-bin PAWS version with the reduced artifact susceptibility of the original 3-bin variation. The new algorithm actively pushes the segment borders away from particularly movement sensitive k-space centers toward k-space peripheries.

In the following comparison of the various PAWS varieties, it is assumed that the overall width of the acceptance window is given. With an n-bin variation, this acceptance window is spanned by n successive clusters of the respiratory position range. As an example, each cluster is assigned a respiratory position range, the width of which corresponds to $1/n^{th}$ of the acceptance window. This differs in comparison, for example, with the Appendix A in the MRM article by Jhooti et al., already cited above, in which the width of the respiratory position range of a cluster is set to be equal to the navigator resolution. With the latter approach, the overall width of the acceptance window is n×the navigator resolution, and increases with the number of bins. This makes it difficult to carry out a fair comparison of different bin-variations.

The efficiency of the new 2-bin variation, described above, is optimal in the sense that as soon as a respiratory position, in a range covered by two adjacent clusters, is measured Ns times, all Ns shots are recorded, and thus the measurement can be stopped. This property is shared by both the new 2-bin variation and the original 2-bin variation, and is distinguished from the original 3-bin variation and the 3-bin variation from the writings by Nuval et al., cited above.

In contrast to the original 2-bin variation, the probability of cluster borders existing in the vicinity of the movement sensitive k-space center is significantly reduced.

This is visible in FIG. 6, in which, as is normal, each line corresponds to a cluster cn. These are disposed in the vertical plane corresponding to their respiratory position range. In the horizontal plane the phase encoding index is ky, or, respectively, in the general depiction, applied as the shot index ns. The grey shaded bars indicate the ky lines or shots, respectively, acquired from a cluster. The upper portion of FIG. 6 reproduces figure 11b of the MRM articles by Jhooti et al. cited above, illustrating the selection of the phase encoding lines of the original 2-bin variation at the end of the measurement. In the lower portion of FIG. 6, the corresponding presentation of the new 2-bin variation is depicted. It can be seen that the number of times a specific respiratory position is measured is the same in both plots. In the original PAWS method depicted in the upper portion, the cluster border is in the vicinity of the k-space center. In the new variation, depicted in the lower portion, it is displaced to a significant degree toward the periphery of the k-space. In FIG. 6, the cluster borders are highlighted in each case with an oval drawn with a broken line.

This problem is largest when the respiratory positions, which are assigned to the two last clusters, are measured with approximately the same frequency, and the central, particularly movement sensitive, shot, having the shot index ns0, or ky=0, respectively, lies precisely in the center of the index range. In this case, the cluster border lies precisely in the k-space center (ky=0). The new version deals with this particularly important case in an optimal manner: the new cluster borders lie at ca.+25% and +75% of the value range, and are thus maximally distanced from the movement sensitive k-space center.

With an asymmetric scanning of the k-space as well, the new 2-bin variation presented herein functions in an optimal manner in the sense that, with the given number of scans occurring for the central cluster, the segment borders are distanced from the central, particularly movement sensitive shot, having a shot index ns0, or ky=0, respectively, to the maximum extent. Thus, the new version, for all practical purposes, always functions better than the original 2-bin version. The reason for this is that the symmetrical distribution of the shots about the central shot ns0 is actively incorporated in the decision process of the algorithm.

Then, and only then, if the number of scans which occur in the final central cluster is less than the number of scans occurring in the final peripheral cluster, a cluster border may exist in the vicinity of the k-space center. In this case, this border may lie closer to the k-space center than with the original version. This case, however, is extremely unlikely with a reasonable distribution of the acceptance window and a static distribution of the respiratory position in the vicinity of the most probable respiratory position, and has not been observed in our numerous measurements made using the new 2-bin variation. By means of an expansion, similar to the modification b), from one of the to documents cited above by Nuval et al., this case can even be entirely prevented: one restricts the termination criteria in such a manner that the central final cluster must have either acquired a minimum percentage of all shots Ns, or the peripheral final cluster must have acquired all shots Ns. It can be seen that the symmetrical distribution about the k-space center in the new 2-bin algorithm is inherent thereto, and need not be stipulated (in contrast to the 3-bin variations in the prior art).

It should also be mentioned that the borderline case of "no respiration" is managed in an optimal manner with the new 2-bin algorithm (as well as with the original version): all shots are acquired from a single cluster, and thus there are no cluster borders, regardless of whether this cluster is a central or a peripheral cluster.

Although modifications and changes may be suggested by those skilled in the art, it is the intention of the inventor to embody within the patent warranted hereon all changes and modifications as reasonably and properly come within the scope of his contribution to the art.

I claim as my invention:
1. A method for acquiring magnetic resonance data from a breathing subject, comprising:
using a processor to subdivide a respiratory position in a respiratory cycle of a breathing subject into a plurality of respiratory position sub-ranges, and to assign each of said respiratory position sub-ranges to a predetermined cluster in a plurality of clusters, each cluster encompasses a predetermined respiratory sub-range of said respiratory position sub-ranges;

operating a magnetic resonance apparatus to acquire a measurement data set, comprising magnetic resonance data from the breathing subject, in a plurality of shots, with the magnetic resonance data of each shot filling a predetermined number of lines in k-space that is less than an entirety of all lines in k-space, and each shot exhibiting a three-dimensional k-space trajectory in k-space, with respectively different shots filling respectively different lines in k-space such that each shot fills a predetermined k-space region;

using said processor to assign a respective shot index to each of said shots that designates a sensitivity of the respective shot to movement by the subject, and assigning said shot indices to the respective shots with adjacent shot indices being assigned to respective shots, among said plurality of shots, that exhibit an incrementally different sensitivity to said movement with a shot exhibiting a highest sensitivity to said movement receiving a shot index in a middle of a total index range;

using said processor to assign a set of shot indices to each of said clusters, said set encompassing a range of adjacent shot indices that is cyclically extended at the index range boundaries such that the highest shot index is adjacent to the lowest shot index and vice versa, said set of shot indices of all clusters initially being empty;

using said processor to assign a start index to each of said clusters, said start index corresponding either to a shot with a high sensitivity to said movement or to a shot with a low sensitivity to said movement, with start positions with high and low sensitivity to said movement alternating between bordering clusters that encompass adjacent respiratory position sub-ranges;

operating said magnetic resonance apparatus to acquire the respective shots by (A) acquiring respiration data from the subject that indicate a current respiratory position of the subject at a time when the respiration data are acquired, (B) using said processor to select a specific cluster, in said plurality of clusters, that has the respiratory sub-range assigned thereto that contains the current respiratory position of the subject, (C) using said processor to select the start index of said specific cluster for a shot to be acquired, if the shot index set of said specific cluster is empty or, if the shot index set of the specific cluster is not empty, selecting a shot to be acquired that has a shot index that does not belong to the shot index set of said specific cluster yet and that has a shot index that borders a shot index that has already been assigned to the shot index set of said specific cluster, and (D) acquiring said shot to be acquired and assigning the shot index of said shot to the shot index set of the specific cluster;

repeating (A), (B), (C) and (D) until the shot index sets of at least two bordering clusters, that encompass adjacent respiratory position sub-ranges of the subject, collectively encompass the shot indices of said shots in said measurement data set;

using said processor to determine said respiratory cycle of the subject, said respiratory cycle comprising at least two respiratory cycle phases;

using said processor to determine, from said shot index sets of said at least two bordering clusters that encompass adjacent respiratory position sub-ranges of the subject, the respiratory cycle phase of the subject during which said magnetic resonance data were acquired; and reconstructing an MR image from magnetic resonance data of said shots assigned to said at least two bordering clusters by executing an image reconstruction algorithm that reconstructs said MR image dependent on the determined respiratory cycle phase.

2. A method as claimed in claim 1 wherein said lines in k-space are oriented along a readout axis of a readout gradient field generated in said magnetic resonance apparatus, and wherein the respective k-space is filled such that different lines acquired by a particular shot are disposed substantially radially in a plane that is perpendicular to said readout axis.

3. A method as claimed in claim 2 comprising using said processor to divide each k-space region into sectors that are defined with respect to a distance thereof from a center of k-space, with a k-space line located in each sector for each of said shots.

4. A method as claimed in claim 3 comprising using said processor to select the respective k-space trajectories so that each k-space trajectory enters data into a k-space line, that is different for each of said shots, in a series corresponding to a neighborhood of the respective sectors in which the respective k-space lines are located, within a respective k-space region.

5. A magnetic resonance apparatus comprising:
a magnetic resonance imaging device;
a processor configured to subdivide a total respiratory position range in a respiratory cycle of a breathing subject into a plurality of respiratory position sub-ranges, and to assign each of said respiratory position sub-ranges to a predetermined cluster in a plurality of clusters, such that each cluster encompasses a predetermined respiratory sub-range of said respiratory position sub-ranges;
said processor being configured to operate said magnetic resonance imaging device to acquire a measurement data set, comprising magnetic resonance data from the breathing subject, in a plurality of shots, with the magnetic resonance data of each shot filling a predetermined number of lines in k-space that is less than an entirety of all lines in k-space, and each shot exhibiting a three-dimensional k-space trajectory in k-space, with respectively different shots filling respectively different lines in k-space such that each shot fills a predetermined k-space region;
said processor being configured to assign a respective shot index to each of said shots that designates a sensitivity of the respective shot to movement by the subject, and assigning said shot indices to the respective shots with adjacent shot indices being assigned to respective shots, among said plurality of shots, that exhibit an incrementally different sensitivity to said movement with a shot exhibiting a highest sensitivity to said movement receiving a shot index in a middle of a total index range;
said processor being configured to assign a set of shot indices to each of said clusters, said set encompassing a range of adjacent shot indices that is cyclically extended at the index range boundaries such that the highest shot index is adjacent to the lowest shot index and vice versa, said set of shot indices of all clusters initially being empty;
said processor being configured to assign a start index to each of said clusters, said start index corresponding either to a shot with a high sensitivity to said movement or a shot with a low sensitivity to said movement, with start positions with high and low sensitivity to said movement alternating between bordering clusters that encompass adjacent respiratory position sub-ranges;

said processor being configured to operate said magnetic resonance imaging device to acquire the respective shots by (A) acquiring respiration data from the subject that indicate a current respiratory position of the subject at a time when the respiration data are acquired, (B) selecting a specific cluster, in said plurality of clusters, that has the respiratory sub-range assigned thereto that contains the respiratory position, (C) selecting the start index of said specific cluster for a shot to be acquired, if the shot index set of said specific cluster is empty or, if the shot index set of the specific cluster is not empty, selecting a shot to be acquired that has a shot index that does not belong to the shot index set of said specific cluster yet and that has a shot index that borders a shot index that is already assigned to said shot index set of said specific cluster, and (D) acquiring said shot to be acquired and assigning the shot index of said shot to the index set of the specific cluster;

said processor being configured to repeat (A), (B), (C) and (D) until the shot index sets of at least two bordering clusters, that encompass adjacent respiratory position sub-ranges of the subject, collectively encompass the shot indices of said shots in said measurement data set;

said processor being configured to determine said respiratory cycle of the subject, said respiratory cycle comprising at least two respiratory cycle phases;

said processor being configured to determine, from said shot index sets of said at least two bordering clusters that encompass adjacent respiratory position sub-ranges of the subject, the respiratory cycle phase of the subject during which said magnetic resonance data were acquired; and said processor being configured to reconstruct an MR image from magnetic resonance data of said shots assigned to said at least two bordering clusters by executing an image reconstruction algorithm that reconstructs said MR image dependent on the determined respiratory cycle phase.

6. A non-transitory, computer-readable data storage medium encoded with programming instructions for operating a magnetic resonance apparatus comprising a magnetic resonance imaging device and a control and processing computer, said storage medium being loaded into the control and processing computer and said programming instructions causing said control and processing computer to:

subdivide a total respiratory position range in a respiratory cycle of a breathing subject into a plurality of respiratory position sub-ranges; and assign each of said respiratory position sub-ranges to a predetermined cluster in a plurality of clusters, each cluster encompasses a predetermined respiratory sub-range of said respiratory position sub-ranges;

operate the magnetic resonance imaging device to acquire a measurement data set, comprising magnetic resonance data from the breathing subject, in a plurality of shots, with the magnetic resonance data of each shot filling a predetermined number of lines in k-space that is less than an entirety of all lines in k-space, and each shot exhibiting a three-dimensional k-space trajectory in k-space, with respectively different shots filling respectively different lines in k-space such that each shot fills a predetermined k-space region;

assign a respective shot index to each of said shots that designates a sensitivity of the respective shot to movement by the subject, and assigning said shot indices to the respective shots with adjacent shot indices being assigned to respective shots, among said plurality of shots, that exhibit an incrementally different sensitivity to said movement exhibiting a shot with a highest sensitivity to said movement receiving a shot index in a middle of a total index range;

assign a set of shot indices to each of said clusters, said set encompassing a range of adjacent shot indices that is cyclically extended at the index range boundaries such that the highest shot index is adjacent to the lowest shot index and vice versa, said set of shot indices of all clusters initially being empty;

assign a start index to each of said clusters, said start index corresponding either to a shot with a high sensitivity to said movement or a shot with a low sensitivity to said movement, with start positions with high and low sensitivity to said movement alternating between bordering clusters that encompass adjacent respiratory position sub-ranges;

operate said magnetic resonance imaging device to acquire the respective shots by (A) acquiring respiration data that indicate a current respiratory position of the subject at a time when the respiration data are acquired, (B) selecting a specific cluster, in said plurality of clusters, that has the respiratory sub-range assigned thereto that contains the current respiratory position, (C) selecting the start index of said specific cluster, if the shot index set of said specific cluster is empty or, if the shot index set of the specific cluster is not empty, selecting a shot to be acquired has a shot index that does not belong to the shot index set of said cluster yet and that has a shot index that borders a shot index that is already assigned to said shot index set of said specific cluster, and (D) acquiring said shot to be acquired and assigning the shot index of said shot to the index set of the specific cluster;

repeat (A), (B), (C) and (D) until the shot index set of at least two bordering clusters, that encompass adjacent respiratory position sub-ranges of the subject, collectively encompasses the shot indices of said shots in said measurement data set;

determine said respiratory cycle of the subject, said respiratory cycle comprising at least two respiratory cycle phases;

determine, from said shot index sets of said at least two bordering clusters that encompass adjacent respiratory position sub-ranges of the subject, the respiratory cycle phase of the subject during which said magnetic resonance data were acquired; and reconstruct an MR image from magnetic resonance data of said shots assigned to said at least two bordering clusters by executing an image reconstruction algorithm that reconstructs said MR image dependent on the determined respiratory cycle phase.

* * * * *